United States Patent [19]

Trogdon

[11] 4,270,863
[45] Jun. 2, 1981

[54] METHOD AND APPARATUS FOR INSPECTING OBJECTS FOR DEFECTS

[75] Inventor: Raymond L. Trogdon, Perrysburg, Ohio

[73] Assignee: Owens-Illinois, Inc., Toledo, Ohio

[21] Appl. No.: 90,215

[22] Filed: Nov. 1, 1979

[51] Int. Cl.³ ................... G06K 9/68; G01N 21/47
[52] U.S. Cl. ................... 356/71; 250/556; 356/448
[58] Field of Search ................... 356/445–448, 356/240, 394, 71; 250/223 B, 555–556, 566; 235/455; 364/581; 340/146.3 AG

[56] References Cited

U.S. PATENT DOCUMENTS

| 4,075,604 | 2/1978 | Degasperi | 356/71 |
| 4,139,779 | 2/1979 | Ehrat | 356/71 |
| 4,150,782 | 4/1979 | Ditmore, Jr. | 250/566 |

Primary Examiner—William H. Punter

Attorney, Agent, or Firm—Steve McLary; M. E. Click; D. H. Wilson

[57] ABSTRACT

Labelled bottles are inspected by illuminating the labelled surface and generating brightness or intensity level signals for a plurality of points on the surface with a photo-sensitive diode array. Each intensity level signal is compared with a stored maximum intensity level and a stored minimum intensity level for the corresponding point. A difference signal is generated if the intensity level is greater than the maximum or less than the minimum intensity level. The difference signals are then weighted and summed to generate a figure of merit for the bottle being inspected. The figure of merit is compared with a predetermined value representing a "good" bottle in order to reject "bad" bottles. The maximum and minimum intensity levels can be generated by passing a plurality of known "good" bottles through the apparatus with labels distributed about the edges of the desired label area.

20 Claims, 5 Drawing Figures

METHOD AND APPARATUS FOR INSPECTING OBJECTS FOR DEFECTS

BACKGROUND OF THE INVENTION

1. Field of the Invention

The invention relates in general to the automatic inspection of objects and in particular to an apparatus and method for inspecting labelled bottles.

2. Description of the Prior Art

In many industries, it is necessary to determine if an object conforms to a predetermined standard. For example, when a label is applied to a package or a container, it is desirable to know that the label was placed in the proper area and that the label has no defect such as a printing error or a tear. Such information is especially important in a process where the labels are automatically applied such as the in-mold labelling of bottles.

Typically, systems for inspecting labelled bottles utilize a photo-sensitive diode array or a television camera to generate signals representing the brightness or intensity levels of the labelled surface. These signals can then be compared with a standard or reference pattern in order to detect missing labels, printing errors, flaws, etc. The standard or reference pattern can be an "ideal" with a set of tolerances or a pattern which has been "learned" by inspecting a number of "good" bottles.

SUMMARY OF THE INVENTION

The present invention concerns a method and an apparatus for inspecting objects and comparing them with a reference to make decisions as to "good" and "bad" with respect to a quality of the object. The invention is particularly useful for inspecting label position and quality for in-mold labelled bottles.

The labelled bottles are moved through an inspection station which includes a bottle position sensor, a camera and a strobe light. The bottle position sensor detects the bottle when it arrives at a location in which the desired labelling area is in front of the camera. Then the strobe light is fired and a photo-sensitive diode array in the camera generates a plurality of signals each representing the gray scale intensity level of a point in the desired labelling area. These brightness level signals can then be compared with a reference pattern to determine if the bottle is "good" or "bad".

The reference pattern is "learned" by inspecting a plurality of bottles with known label positions. The bottles typically represent labels distributed about the edges of the desired labelling area. A maximum and a minimum intensity level is stored for each point as generated by the reference bottles. As a bottle is inspected, the intensity level signal for each point is compared with the stored maximum and minimum intensity levels for that point. If the signal is greater than the maximum or less than the minimum, a difference signal is generated representing the absolute value of the magnitude difference between the signal and the maximum and minimum levels respectively. The difference signals are summed and compared with a predetermined value representing a minimum "good" bottle. If, at any time during the inspection, the sum exceeds the predetermined value, the bottle is "bad". The discovery of a "bad" bottle can actuate a display and/or warning and can also be utilized to control a reject mechanism.

Not all difference signals have the same importance. For example, a relatively large difference at a relatively small number of points could represent a tear, whereas a relatively small difference at a relatively large number of points could represent a tonal variation having the same difference sum. If it is desired to assign more importance to a tear type of defect, larger differences can be weighted more than small differences. Thus, the magnitude of larger difference signals can be increased and the magnitude of smaller difference signals can be decreased. In the present invention, the difference signal is in binary form such that the bits are shifted to the left for large differences, shifted to the right for small differences, and not shifted for medium differences.

DESCRIPTION OF THE PREFERRED EMBODIMENT

Figure 1:
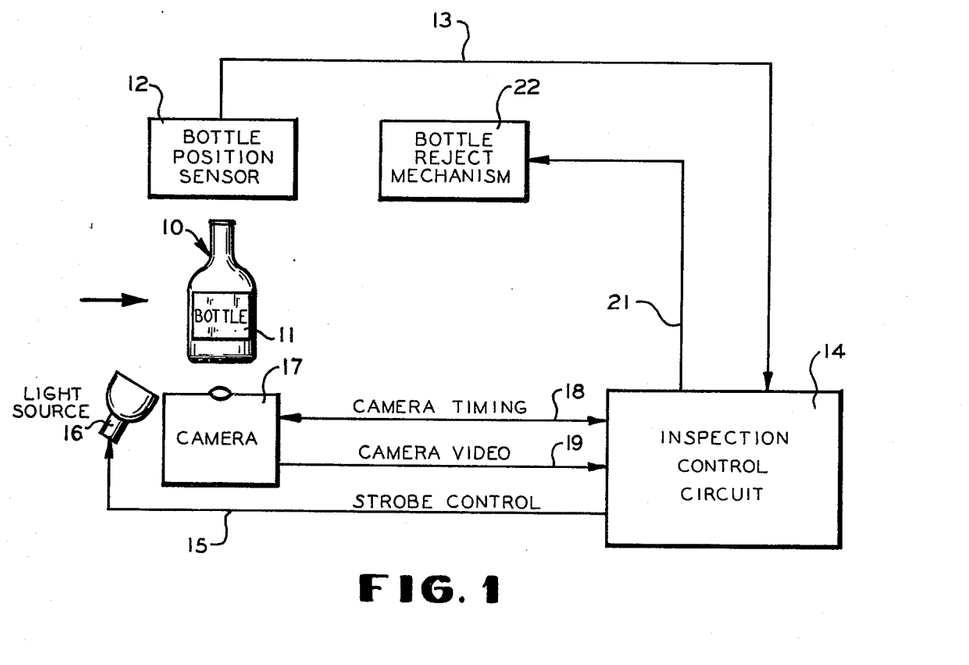
FIG. 1 is a block diagram of a bottle inspection system according to the present invention.

There is shown in FIG. 1 a block diagram of a system for inspecting labels on bottles produced by an in-mold labeling process. In an in-mold labelling process, labels are positioned in the mold before the bottle is formed. When the bottle is blown, the bottle material, typically plastic, flows over the back and edges of the label. As the bottle material cools, the label adhers to and is recessed in the side of the bottle. The inspection system shown in FIG. 1 automatically inspects the bottles to determine whether the labels have been properly positioned or printed. When the system detects a "bad" bottle, the system generates the appropriate signals for identifying the bottle and/or rejecting the bottle subsequent to the inspection process.

Referring to FIG. 1, a bottle 10 has a label 11 affixed to a side thereof. The bottle is carried to the inspection system by suitable means such as a conveyor (not shown). A bottle position sensor 12 detects the bottle as it reaches the inspection position and generates a signal on a line 13 to an inspection control circuit 14 when the bottle 11 is properly positioned for inspection. Typically, the sensor 12 detects the leading edge of the bottle 10. The inspection control circuit 14 controls the inspection process and generates the appropriate reject signals if a "bad" bottle is detected. As will be discussed, the inspection control circuit 14 can be either a discrete conponent circuit or a microprocessor based circuit.

When the bottle 10 has been properly positioned for inspection, the control circuit 14 generates a strobe control signal on a line 15 to strobe a light source 16 which is directed at the area on the side of the bottle where the label 11 should be positioned. The light reflected from the bottle and/or label is detected by a camera 17 which receives timing signals on a line 18 from the control circuit 14. The camera 17 can be a model TN 2200 manufactured by General Electric of Syracuse, N.Y. or a MC520C manufactured by Reticon of Sunnyvale, Calif. or any similar camera. Such a camera includes a light sensitive diode array in which each diode generates a signal having a magnitude proportional to the gray scale brightness or intensity level of the point on the bottle or label being looked at by the diode. The General Electric camera has a one hundred twenty-eight by one hundred twenty-eight array and the Reticon camera has a one hundred by one hundred array.

The video information generated by the camera 17 is supplied to the control circuit 14 on a line 19. The timing signals on the line 18 control the number of and the order in which the diodes in the camera 17 transmit the video information on the line 19. Typically, commercially available cameras must be read sequentially, diode-by-diode, in a predetermined order such as horizontal lines starting in one corner of the array and ending in the opposite corner. The inspection control circuit can generate clock pulses to determine the reading frequency and the camera can return end of line and end of frame (array) signals.

The video information can then be converted into digital form and stored in a memory (not shown). The control circuit 14 then compares the video information from the camera 17 with a set of predetermined brightness levels which have been stored in a memory (not shown). The set of predetermined brightness levels represent a reference pattern for defining a "good" bottle. If the control circuit 14 detects a "bad" bottle, the circuit 14 generates a bottle reject signal on a line 21 to a bottle reject mechanism 22 to reject the "bad" bottle from the conveyor.

Figure 2:
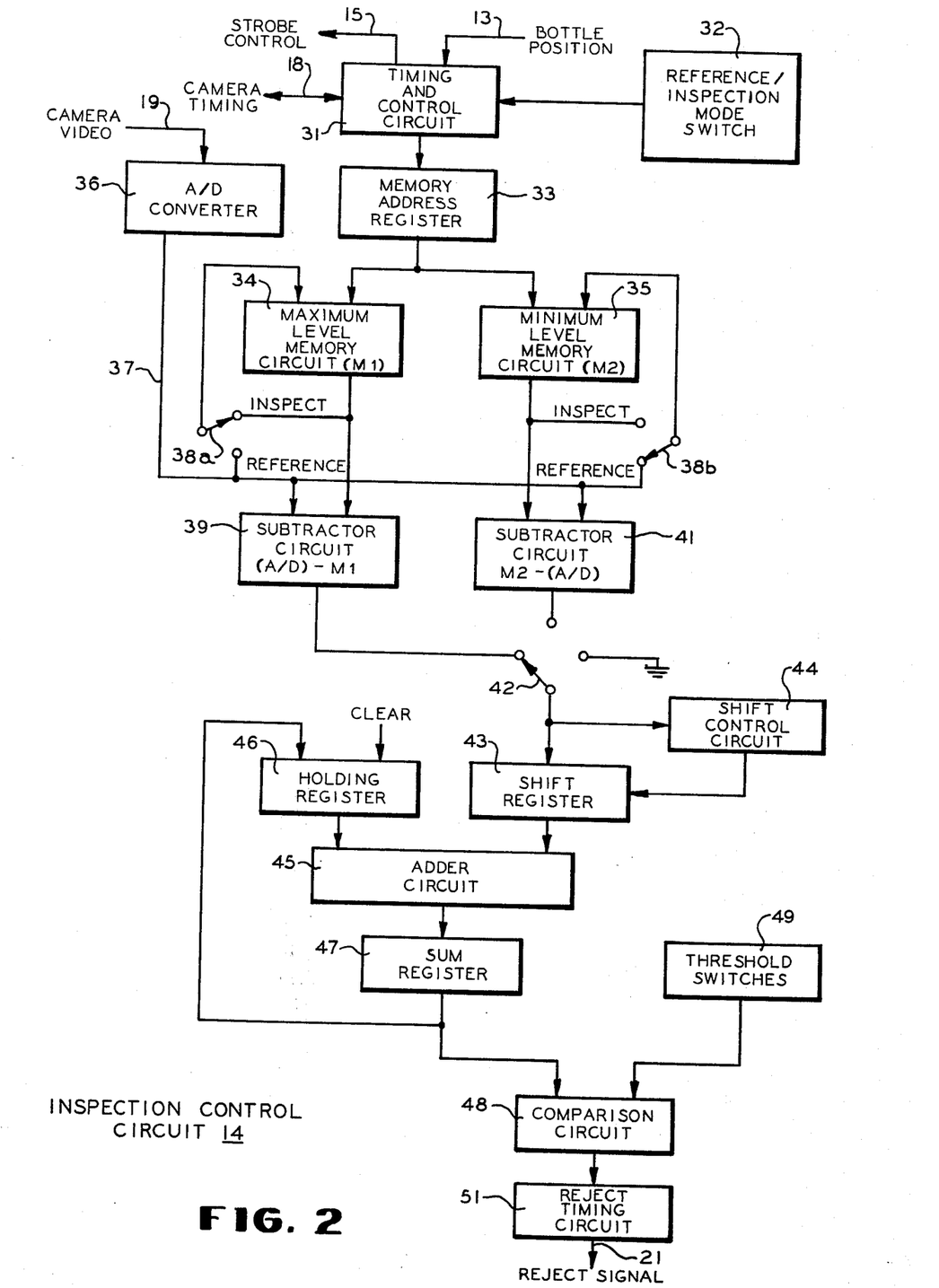
FIG. 2 is a block diagram of the inspection control circuit shown in FIG. 1.

There is shown in FIG. 2 a block diagram of the inspection control circuit 14 of FIG. 1. As will be discussed, the circuit of FIG. 2 operates in two modes, a reference mode and an inspection mode. In the reference mode, "good" bottles are strobed and intensity levels are stored in a memory to establish the reference levels required for inspection. In the inspection mode, individual bottles are inspected to determined if the labels fall within the set of levels stored in the reference mode.

In FIG. 2, a timing and control circuit 31 receives a control signal from a reference/inspection mode switch 32 which sets the timing of the circuit in accordance with the desired mode. The circuit 31 receives the bottle position signal on the line 13 and generates a strobe control signal on the line 15 and camera timing and control signals on the line 18. The circuit 31 is also utilized to control a memory address register 33 for addressing a maximum level memory circuit (M1) 34 and a minimum level memory circuit (M2) 35.

An A/D converter 36 receives the camera analog video signals on the line 19 and generates a digitized signal on a line 37 representing the intensity level sensed by each diode. If the circuit of FIG. 2 is operating in the reference mode, one of a pair of switches 38a and 38b applies the digital signal on the line 37 to the inputs of one of the memory circuits 34 and 35. If the circuit is operating in the inspect mode, the switches 38a and 38b remain in the inspect position. Typically, the switches 38a and 38b can be electronic switches which are controlled by the timing and control circuit 31.

Before discussing the remaining portion of FIG. 2, the operation of the circuit in the reference mode will be explained. The reference mode is utilized to establish a maximum reference and a minimum reference value for each point on the bottle and/or label corresponding to a diode in the array. The maximum and minimum reference values define an allowable range over which the brightness level at that point can vary and still be considered satisfactory with respect to a "good" bottle.

Typically, a group of bottles having "good" labels are utilized to determine the reference levels. The first "good" bottle is properly positioned in front of the camera and the light source is strobed. The video information is converted to digital form and applied to memory circuits 34 and 35. Each of the memory circuits 34 and 35 has a separate memory location for storing the intensity level value of each point or diode. For example, each diode intensity value can be represented by a four bit binary word which is stored as a word in the memory. When the first reference bottle is strobed, memory circuits 34 and 35 are loaded with the intensity value for each diode. Thus, after the first bottle is strobed, the maximum reference values will be equal to the corresponding minimum reference values.

The line 37 is connected to the inputs of a pair of subtractor circuits 39 and 41. The subtractor circuit 39 also has an input connected to an output of the maximum level memory circuit 34 and the subtractor circuit 41 also has an input connected to an output of the minimum level memory 35. The switch 38a has an inspect contact connected to the output of the memory circuit 34, a reference contact connected to the line 37, and a moving contact connected to an input to the memory circuit 34. The switch 38b has an inspect contact connected to the output of the memory circuit 35, a reference contact connected to the line 37, and a moving contact connected to an input to the memory circuit 35.

Assuming that the memory circuits are cleared with zero brightness level values, each diode intensity value for the first "good" bottle will generate a positive polarity output signal from the subtractor circuit 39 which subtracts the stored value from the diode value. The timing and control circuit responds by switching the switch 38a to the reference position to store the diode intensity value. The subtractor circuit 41, which subtracts the diode value from the stored value, will generate a negative polarity output signal for each diode and the circuit 31 will maintain the switch 38b in the inspect position to prevent the storage of any diode intensity values.

The minimum level memory circuit 35 must also be loaded with the diode intensity values from the first "good" bottle. This could be accomplished by "clearing" the memory circuit 41 by storing a predetermined high intensity value for each of the points. Then, each diode intensity value for the first "good" bottle would generate a positive polarity output signal from the subtractor circuit 41 to switch the switch 38b to the reference position.

As subsequent "good" bottles are strobed, the diode intensity values are compared with the corresponding maximum and minimum reference intensities stored in the memory circuits 34 and 35. If the intensity value from a diode is greater than the corresponding maximum reference value, this intensity will become the new maximum reference value for that particular point as the switch 38a is switched to the reference position. Similarly, if the diode intensity value is less than the corresponding minimum reference value, this intensity will become the new minimum reference value for that point as the switch 38b is switched to the reference position. If this intensity value falls between the corresponding maximum and minimum reference values, the reference values will remain the same.

When all of the reference bottles have been strobed, the memory circuits 34 and 35 will define an allowable range over which the diode intensity value can vary. The reference inspection mode switch 32 is then activated to switch the circuit of FIG. 2 to the inspection mode. The activation of the switch 32 to the inspection mode automatically adjusts the timing of the circuit 31 and sets the switches 38a and 38b to the inspect position. Typically, the "good" bottles for the reference mode of operation are selected with the labels positioned to define the edges of an area of acceptable positions for the labels.

When in the inspection mode, the circuit 31 functions to control the memory address register 33 and the camera such that each diode in the array has its signal compared with the corresponding stored maximum and minimum reference values. The bottle position signal on the line 13 signals the circuit 31 when a bottle is in position for inspection. The circuit 31 responds by generating a signal on the line 15 to strobe the light source and initiating the comparison operation.

The subtractor circuits 39 and 41 are utilized to perform the comparison operation. The subtractor circuits 39 and 41 each receive the digital signal representing the intensity of a point on the bottle and label being inspected on the line 37. The circuit 39 subtracts the corresponding maximum reference value from the inspected point intensity ((A/D)M1) while the circuit 41 subtracts the inspected point intensity from the corresponding minimum reference value (M2(A/D)). Thus, if the intensity of the inspected point is outside of the allowable intensity range, the output of one of circuits 39 or 41 will be a positive number. Otherwise, if the inspected intensity is within the allowable range, the outputs of both the circuits 39 and 41 will be negative numbers or zero.

A switch 42 is connected between the outputs of the subtractor circuits 39 and 41 and the input of a shift register 43. The switch 42 is controlled in accordance with the results of the comparison operation performed by the circuits 39 and 41. If either the circuit 39 or the circuit 41 generates a positive difference signal indicating that the inspected intensity is within its range, the switch 42 is connected to a ground potential to load the shift register with a zero difference signal. The switch 42 can be an electronic switch which is controlled by polarity output signals generated by the circuits 39 and 41.

The difference signal supplied to the shift register 43 through the switch 42 is also an input to a shift control circuit 44. The shift control circuit 44 senses the magnitude of the difference signal and generates an output signal to control the shift register 43.

The shift register 43 and the shift control circuit 44 function to increase the significance of large errors in intensity, and to decrease the significance of small errors in intensity. It is important to note that it is more likely that a serious label flaw exists when a relatively small number of points are in error by a large amount than when a relatively large number of points are in error by a small amount. For example, a tear in the label will result in a relatively small number of points each having a large intensity error, while a slight difference in tonation of the label will result in a large number of points each having a small intensity error. Thus, while the bottle with the torn label is clearly a "bad" bottle, the bottle having a label of slightly different tonation may be acceptable.

The present invention distinguishes between a "bad" bottle and a "good" bottle by increasing the significance of relatively large errors in point intensity and decreasing the significance of relatively small errors in point intensity. For example, if the intensity difference is represented by a four bit binary number, the shift control circuit 44 can shift the difference signal in the register 43 one bit to the left to increase the significance, or the circuit 44 can shift the signal one bit to the right to decrease the significance. It should be noted that for some differences it may be desirous not to perform any shifting operation, for example, when the difference falls in the midrange between large and small differences.

The shift register 43 then generates an error signal, which is the difference signal after the shifting operations have been performed, to an adder circuit 45. The circuit 45 adds the error signal to the value stored in a holding register 46 and loads the total into a sum register 47. The value in the sum register 47 is supplied the holding register 46 to replace the value previously stored in the holding register. The value in the sum register 47 represents the total of all the error signals generated by the shift register 43 during the inspection of a particular bottle. Before each bottle is inspected, the holding register 46 receives a clear signal which can be generated by the circuit 31 to clear the register to a zero total.

Each time a point is inspected, the contents of the sum register 47 is compared by a comparison circuit 48 with a threshold setting as determined by threshold switches 49. If the total error in the sum register 47 exceeds the threshold setting, a "bad" bottle has been detected and the comparison circuit 48 generates a signal to a reject timing circuit 51. The timing circuit 51 then generates a reject signal on the line 21 to the bottle reject mechanism when the bottle is in the proper position to be rejected. If the error value in the sum register 47 is less than the threshold setting of the switches 49 after all the points have been inspected, the bottle is considered "good". The timing and control circuit 31 then adjusts the timing to begin the inspection of a new bottle.

Figure 3:
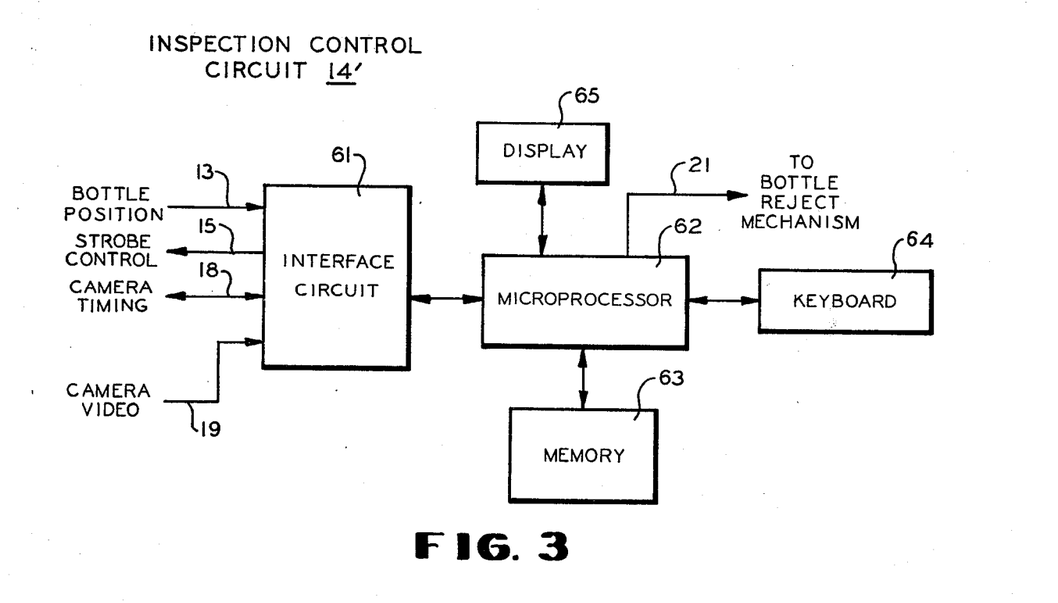
FIG. 3 is a block diagram of an alternate embodiment of the inspection control circuit shown in FIG. 1.

There is shown in FIG. 3 an alternate embodiment of the inspection control circuit 14 of FIG. 1. As was the case with the inspection circuit of FIG. 2, the circuit 14' of FIG. 3 operates in two modes, a reference mode and an inspection mode. A detailed discussion of the two modes of operation will follow the discussion of FIG. 3.

An interface circuit 61 is utilized to interface a microprocessor 62 to the bottle position sensor 12, the light source 16, and the camera 17. The microprocessor 62 is connected to a memory 63 which is utilized to store the maximum and minimum reference intensity values. The operating parameters of the system are supplied to the microprocessor 62 by an operator via a keyboard 64. A display 65 is connected to the microprocessor and can be utilized to display such information as operating mode and "good" or "bad" bottles.

Figure 4:
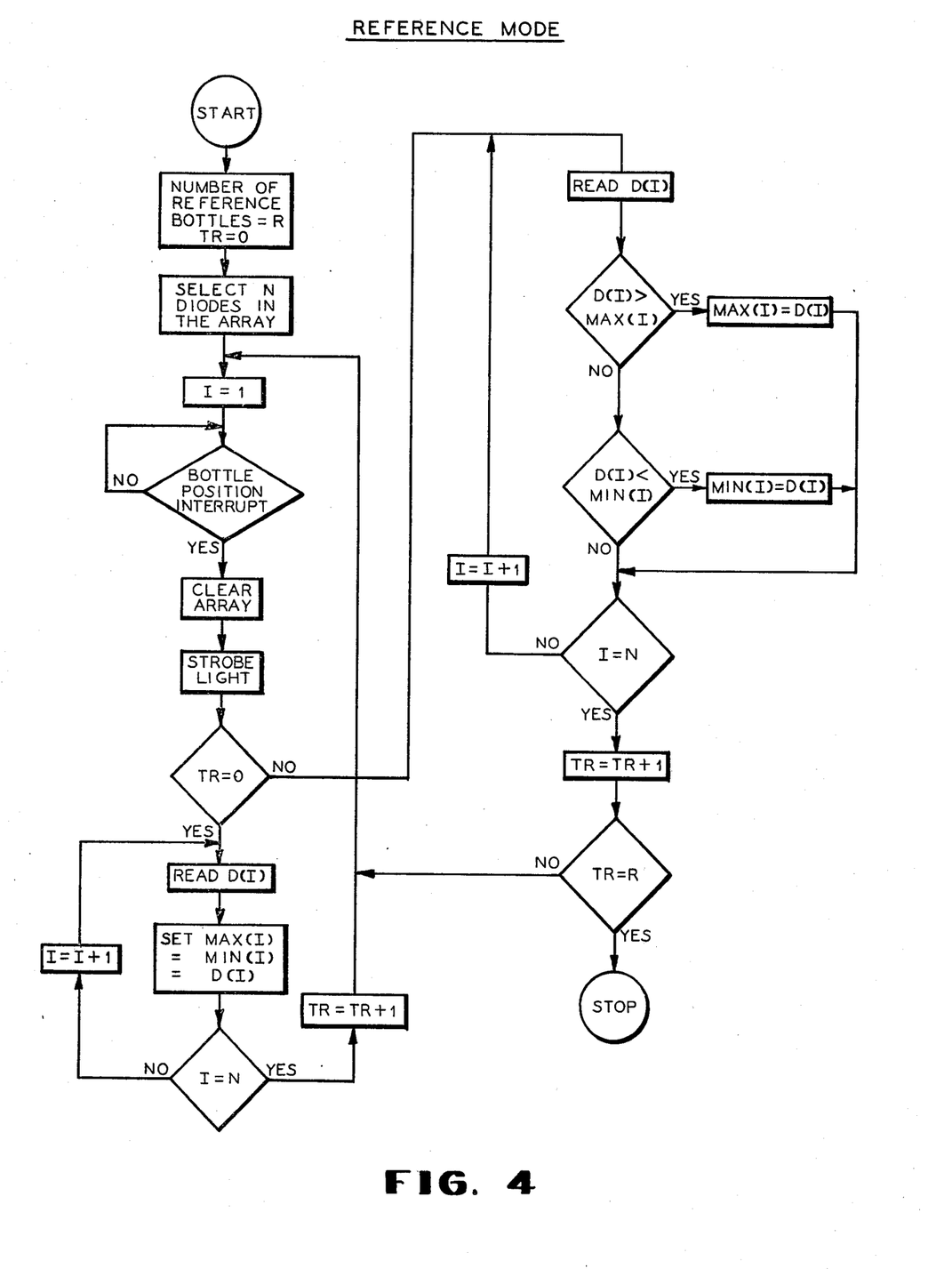
FIG. 4 is a flow diagram of the reference mode of operation of the bottle inspection system shown in FIG. 1.
Figure 5:
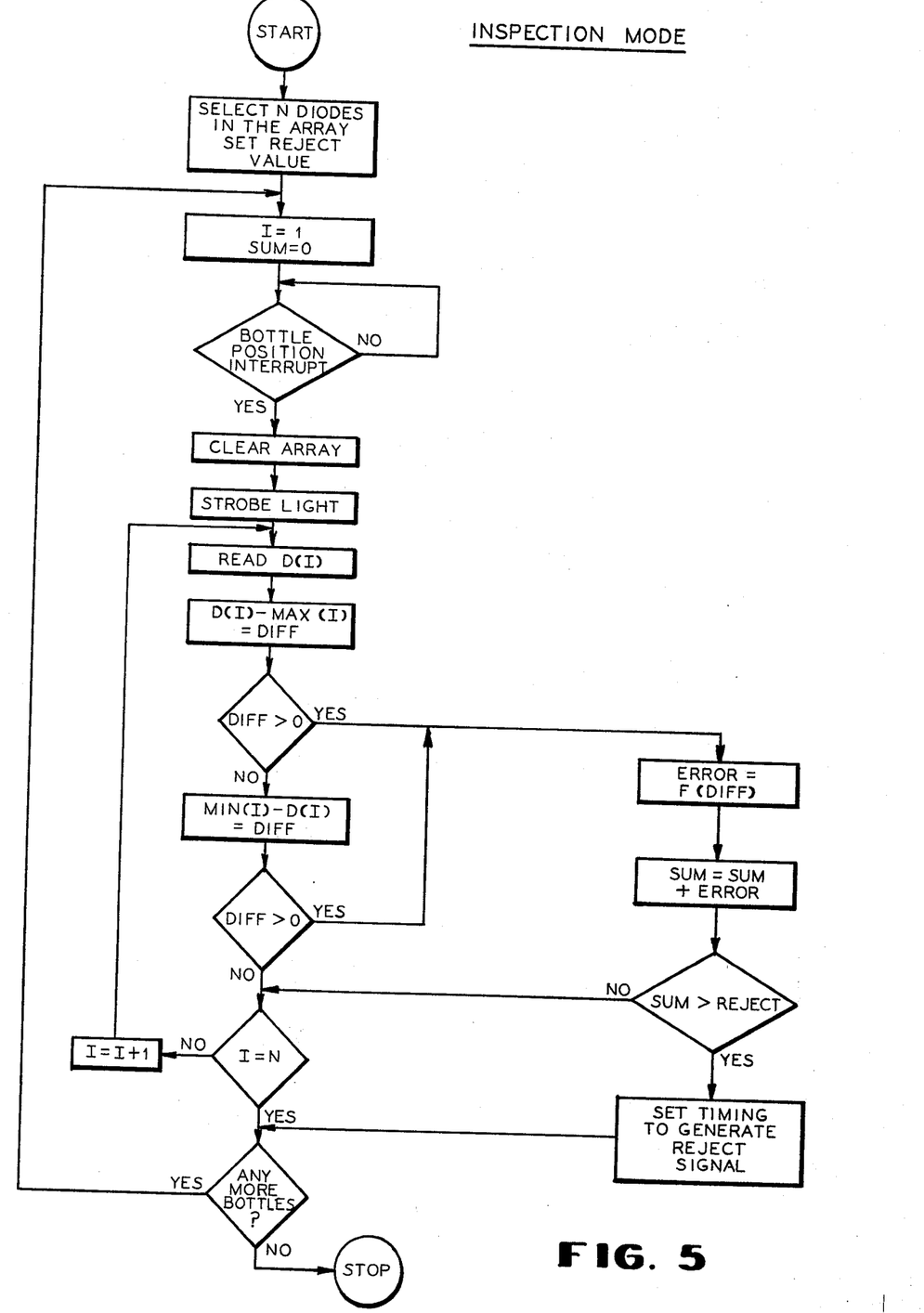
FIG. 5 is a flow diagram of the inspection mode of operation of the bottle inspection system shown in FIG. 1.

There are shown in FIGS. 4 and 5 simplified flow diagrams of the operation of the microprocessor inspection circuit of FIG. 3. The reference mode program is shown in FIG. 4, and the inspection mode program is shown in FIG. 5. As will be discussed, the operation of the circuit of FIG. 3 is similar to the operation of the inspection circuit of FIG. 2.

The reference mode program shown in FIG. 4 is initiated at a circle "start". The program then enters a processing function "NUMBER OF REFERENCE BOTTLES = R TR = 0" which includes instruction for reading from the keyboard the number R of reference bottles to utilized and setting a reference bottle counter TR equal to zero. A processing function "SELECT N DIODES IN THE ARRAY" includes instructions for reading the number N and position of the diodes to be read. Next, a processing function "I = 1" sets a diode counter and the system is ready to build a reference pattern.

The inspection circuit shown in FIG. 3 can also be operated by utilizing a switch to select the reference mode. The circuit will then build a reference pattern from any number of bottles which are sent past the inspection station as long as the switch remains in the reference position. Such operation would eliminate the need for the reference bottle counter "TR" and for entering the number of reference bottles to be utilized. Different types of cameras may require different types of clearing operations. The above identified General Electric camera has such a large diode array that it is not practical to clear the array between the detection of a bottle and the reading of that bottle. Therefore, the array is read continuously which clears each diode as it is read. When a bottle is detected, the present line is completed and the strobe light is fired before the next line is started. Then, the entire array is read starting with that next line. With the Reticon camera, the array can be held in a cleared state. When a bottle is detected, the array is released and the strobe light is fired. A Reticon MC 510 camera has a thirty-two by thirty-two array which can be cleared by reading and ignoring the results at typical conveyor speeds.

A decision point "BOTTLE POSITION INTERRUPT" looks for a bottle position signal on the line 13. In the absence of such a signal, the program branches at "NO" and loops through the decision point. If the signal is received, the program branches at "YES" to a processing function "CLEAR ARRAY" and then to a processing function "STROBE LIGHT". Thus, the diode array is cleared of any previous readings and the strobe light is actuated to generate a new set of readings.

A decision point "TR = 0" checks for the first reference bottle which causes a branch at "YES" to set the maximum and minimum memories. A processing function "READ D(I)" includes instructions for reading the "I" diode intensity level. A processing function "SET MAX (I) = MIN (I) = D(I)" includes instructions for setting the corresponding maximum and minimum memory locations equal to the detected intensity value. A decision point "I = N" checks for the last diode to be read. If "I" is not the last diode, the program branches at "NO" to a processing function "I = I + 1" to increment the diode counter and return to the "READ D(I)" processing function for the next diode. If "I = N", the program branches at "YES" to a corresponding function "TR = TR + 1" to increment the reference bottle count and return to the processing function "I = 1" and wait for the next reference bottle.

For each reference bottle after the first, "TR" will be greater than zero and the program will branch from the decision point "TR = 0" at "NO" to a processing function "READ D(I)" which includes instructions for reading the "I" diode intensity level. Next, a decision point "D(I) > MAX(I)" checks for an intensity level greater than the stored maximum intensity level. If the new level is greater than the stored level, the program branches at "YES" to a processing function "MAX(I) = D(I)" which includes instructions for replacing the stored level with the new level. If the intensity level is equal to or less than the stored maximum intensity level, the program branches at "NO" from "D(I) > MAX(I)" to a decision point "D(I) < MIN(I)". If the new intensity level is less than the stored minimum intensity level, the program branches at "YES" to a processing function "MIN(I) = D(I)" which includes instructions for replacing the stored level with the new level.

If the new level is equal to one or between both of the stored levels, the program branches at "NO" from "D(I) < MIN(I)" to a decision point "I = N". Both the "MAX(I) = D(I)" and th "MIN(I) = D(I)" processing functions also lead to this decision point. If the last diode has not been read, the program branches at "NO" to a processing function "I = I + 1" to increment the diode counter and return to the "READ D(I)" processing function for the next diode. If "N = I", the program branches at "YES" to a processing function "TR = TR + 1" to increment the reference bottle counter. Next, the program enters a decision point "TR = R" to check for the last bottle. If the last bottle has not been read, the program branches at "NO" to return to the processing function "I = 1" and wait for the next reference bottle. If the last bottle has been read, the program branches at "YES" to exit the reference mode at a circle "STOP".

As stated above, the reference bottle counter "TR" can be eliminated if the inspection circuit is switched to a continuous reference mode. Then, the program would branch at "YES" from "I = N" to the input of the "BOTTLE POSITION INTERRUPT" decision point. The program would then loop until the next reference bottle enters the inspection station.

The inspect mode operation of the present invention is shown in the flow diagram of FIG. 5. The program is initiated at a circle "START" and then enters a processing function "SELECT N DIODES IN THE ARRAY SET REJECT VALUE". This processing function includes instructions for setting the position and number "N" of the diodes to be read and a reject value. The program then enters a processing function "I = 1 SUM = 0" to initialize the diode counter "I" and set to zero the summation of error values of differences from the stored reference levels. The program then enters a decision point "BOTTLE POSITION INTERRUPT" to await a bottle position signal by looping at "NO".

When the bottle position signal is generated, the program branches at "YES" to processing functions "CLEAR ARRAY" and "STROBE LIGHT" to clear the diode array of old intensity levels and light the bottle to obtain new intensity levels. Next, the program enters a processing function "READ D(I)" which includes instructions for reading the (I) diode intensity level. The program then enters a processing function "D(I) − Max(I) = DIFF" to obtain the difference in intensity levels between the new value and the stored maximum value. The program enters a decision point "DIFF > 0" to determine if the value of "DIFF" is positive indicating that the intensity "D(I)" is greater than the corresponding maximum reference intensity. If "DIFF" is not greater than zero, the program branches at "NO" to a processing function "MIN(I) − D(I) = -DIFF" to determine the difference between the stored minimum reference intensity "MIN(I)" and the corresponding new intensity level "D(I)". Next, the program enters a decision point "DIFF>0" to determine if the value of "DIFF" is positive, indicating that the intensity "D(I)" is less than the corresponding minimum reference value. If "DIFF" is not less than "MIN(I)", the program branches to "NO" to a decision point "I=N" to check if all the diode intensities have been compared with the corresponding maximum and minimum reference intensities.

If the value of "DIFF" is greater than zero, indicating that the intensity "D(I)" is outside its allowable range, the program branches from one of the two decision points "DIFF>0" at "YES" to a processing function "ERROR=F(DIFF)". This processing function includes instructions for determining the value of "ERROR" as a function of the value of "DIFF". As was the case for the inspection circuit of FIG. 2, the value "ERROR" is determined by increasing the significance of large differences in intensity levels, while decreasing the significance of small differences in intensity levels. Next, the program enters the processing function "SUM=SUM+ERROR" to calculate the value of "SUM" which is the total of all the "ERROR" values obtained in the inspection of this particular bottle.

The program then enters a decision point "SUM REJECT" to determine if the "SUM" value exceeds the threshold value "REJECT" indicating that the bottle being inspected is "bad". If the bottle is not "bad", the program branches at "NO" to the decision point "I=N". If all the intensity levels have not been compared with the reference values, the program branches from "I=N" at "NO" to enter the processing function "I=I+1" to increment the variable "I". The program then returns to the processing function "READ D(I)" to perform the comparison operation on the next diode.

If "I=N", indicating that all the points on the bottle have been inspected and that the bottle is "good", the program branches from "I=N" at "YES" to a decision point "ANY MORE BOTTLES?" which includes instructions to determine if there are any more bottles to be inspected.

If a "bad" bottle has been detected, the program branches from "SUM REJECT" at "YES" to a processing function which includes instructions for generating a reject signal to the bottle reject mechanism 22 when the bottle is to be rejected. The program then enters the decision point "ANY MORE BOTTLES?".

If more bottles are to be inspected, the program branches at "YES" to return to the processing function "I=1 SUM=0". If all the bottles have been inspected, the program branches at "NO" to exit the program at a circle "STOP".

In certain instances, it may be desirable to conduct other tests on the bottles being inspected. For example, the diode array can be divided into smaller areas such as groups of sixteen by sixteen diodes. A maximum and a minimum intensity reference value can be obtained by summing the intensity values for the small arrays each time a referenced bottle is read. These maximum and minimum values can then be utilized the same way that similar values for individual diodes are utilized. The differences generated when bottles are inspected may or may not be weighted and added to the weighted differences for individual diodes to obtain the "SUM" for comparison purposes.

The smaller diode arrays are more sensitive to localized label flaws in the presence of label position errors. For example, the combination of a flaw in the label and a shift in position of the label could produce individual intensity values which are intermediate to the maximum and minimum reference intensity values, thereby masking both defects. If the diode array is divided into four quadrants, for example, a summed intensity value can be generated for each quadrant. One method of utilizing these sums is to multiply the largest number by four, subtract the other three numbers and compare the result with the sum of all four numbers. The larger total can then be compared with a reject value. Another method would be to subtract the total of all four sums from four times the largest sum as a modification of the above-described method. These methods have more sensitivity to flaws located in one or two of the quandrants than does the method of looking only at individual diodes.

The division of the diode array into smaller diode arrays is also useful for inspecting labels having many lines of printed matter. If a label has a printing defect or is simply not aligned properly, one of the smaller diode arrays will be sensitive to such a defect whereas, the label as a whole could fall into the acceptable range.

It is also possible that after the system has been running in the inspection mode, it may be desirable to modify the reference values with current production data. The system can be switched into the reference mode without setting the memory values to the intensity levels for the first reference bottle. The system will then add data to the stored reference values if new maximum and minimum values are detected. This feature is useful if the label position drifts during a production run but remains within an acceptable area. After the new reference pattern is built, the system can be returned to the inspection mode.

In summary, the present invention concerns a method and an apparatus for inspecting objects for defects by comparing the gray scale brightness intensity values for the object with stored maximum and minimum intensity values defining a range of acceptable objects. A gray scale signal is generated for each of a plurality of points on the object and the magnitude of the signal is compared with the stored maximum and minimum intensity values. If the gray scale signal is outside the range, a difference signal is generated having a magnitude proportional to the amount by which the signal falls outside the range. Larger difference signals are given greater weight and the weighted difference signals are summed to obtain a figure of merit for the object being inspected.

The present invention can also be utilized with a camera which is a linear diode array. The light source 16 can be a continuous light source. The diode array is then read each time the bottle moves a predetermined distance past the diode array. The present invention can also utilize only one intensity level, maximum or minimum. For example, if the label has a light background with dark text, the maximum intensities can be utilized. The system would not be as sensitive to position change as when both maximum and minimum intensities are utilized.

In accordance with the provisions of the patent statutes, the principle and mode of operation of the invention have been described and illustrated in its preferred embodiment. However, it must be understood that the invention can be practiced otherwise than as specifically illustrated and described without departing from its spirit or scope. The invention can be utilized to inspect any type of object for a gray scale pattern.

What is claimed is:

1. In an apparatus for the automatic comparison of an object with a reference representing selected points on a standard object including a light source for illuminating a surface of the object including the selected points and a photo-sensitive detector for generating a gray scale brightness intensity level signal for each of the selected points, the improvement comprising:
   means for storing a maximum and a minimum intensity level for each of the selected points;
   means for generating a difference signal for each of the selected points representing the difference between the intensity level signal and said maximum intensity level when the intensity level signal is greater than said maximum intensity level and representing the difference between said minimum intensity level and the intensity level signal when the intensity level signal is less than said minimum intensity level;
   means for weighting said difference signals in accordance with the magnitudes thereof; and
   means for summing said difference signals to generate an indication of the comparison of the object with the reference.

2. The apparatus according to claim 1 wherein said means for generating a difference signal includes means for generating a first output signal representing the difference between the intensity level signal and said maximum intensity level, means for generating a second output signal representing the difference between said minimum intensity level and the intensity level signal, and means for generating said difference signal when one of said first and second output signals is positive.

3. The apparatus according to claim 1 wherein said means for weighting increases the magnitude of said difference signal when the magnitude of said difference signal is greater than a first predetermined value.

4. The apparatus according to claim 3 wherein said means for weighting decreases the magnitude of said difference signal when the magnitude of said difference signal is less than a second predetermined value lower than said first predetermined value.

5. In an apparatus for automatically inspecting labels on bottles including a light source for illuminating a surface of the bottle in the area of the desired position for the label and an array of photo-sensitive detectors, each detector generating a gray scale brightness intensity level signal representing the brightness level of a point on the illuminated surface, the improvement comprising:
   means for storing a maximum and a minimum intensity level signal for each point in the detector array;
   means for generating a difference signal representing the intensity level difference when the intensity level is greater than the corresponding maximum intensity level or is less than the corresponding minimum intensity level;
   means for weighting said difference signals in proportion to the intensity level difference;
   means for generating a total signal representing the sum of said weighted difference signals; and
   means for comparing said total signal with a predetermined reference value representing a quality of the bottle and label being inspected.

6. The apparatus according to claim 5 wherein said means for storing includes a memory circuit having a separate storage location for each of said maximum and minimum intensity level signals.

7. The apparatus according to claim 5 wherein said means for generating a difference signal includes means for generating a first subtraction signal representing the difference in magnitudes of the intensity level signal and the corresponding one of said maximum intensity level signals and generating a second subtraction signal representing the difference in magnitudes of the corresponding one of said minimum intensity level signals and the intensity level signal, and means responsive to one of said first and second subtraction signals having a positive polarity for generating said difference signal.

8. The apparatus according to claim 5 wherein said means for weighting increases the magnitude of said difference signal when the magnitude of said difference signal is greater than a first predetermined value.

9. The apparatus according to claim 8 wherein said means for weighting decreases the magnitude of said difference signal when the magnitude of said difference signal is less than a second predetermined value lower than said first predetermined value.

10. The apparatus according to claim 5 wherein said difference signals are in binary form and said means for weighting includes means responsive to the magnitude of said difference signals for shifting the bits of said binary difference signals to generate said weighted difference signals.

11. The apparatus according to claim 5 wherein said means for comparing includes means for selecting said predetermined reference value.

12. The apparatus according to claim 5 wherein said maximum and minimum intensity level signals are generated by inspecting a plurality of reference bottles and generating intensity level signals therefor and including means responsive to said difference signals for storing each of said intensity level signals as a maximum intensity level signal if the magnitude of said intensity level signal is greater than the magnitude of said maximum intensity level signal presently stored and as a minimum intensity level signal if the magnitude of said intensity level signal is less than the magnitude of said minimum intensity level signal presently stored.

13. A method of inspecting an object by comparing the gray scale brightness intensity level of selected points on the object with a maximum intensity level and a minimum intensity level for each point comprising the following steps:
   a. generating a gray scale brightness intensity level signal for a selected point on the object;
   b. generating a difference signal having a magnitude proportional to the difference between said intensity level signal magnitude and the maximum intensity level magnitude for the selected point when said intensity level signal is greater than the maximum intensity level;
   c. generating a difference signal having a magnitude proportional to the difference between said intensity level signal magnitude and the minimum intensity level for the selected point when said intensity level signal is less than the minimum intensity level;
   d. weighting said difference signal by a factor related to the magnitude of said difference signal;
   e. repeating steps a. through d. for all of the selected points; and
   f. comparing a total of all said weighted difference signals with a predetermined value representing a desired characteristic of the object.

14. The method according to claim 13 including the step of indicating a "bad" object when said total exceeds said predetermined value.

15. The method according to claim 14 wherein said indicating step includes terminating step a. through e.

16. The method according to claim 13 wherein step d. includes increasing the magnitude of said difference signal when the magnitude is greater than a first predetermined value.

17. The method according to claim 16 wherein step d. includes decreasing the magnitude of said difference signal when the magnitude is less than a second predetermined value less than said first predetermined value.

18. A method of inspecting labels on bottles utilizing an inspection apparatus having means for generating a plurality of signals each having a characteristic representing the gray scale brightness intensity level of a point in a field corresponding to a desired label position area on the bottle and means for rejecting the bottle in response to a rejection signal, the method comprising:
   a. generating the gray scale signals for a plurality of sample bottles having labels at selected positions in the desired label position area;
   b. storing a list of the maximum intensity level for each point in the field by selecting the signal having the maximum value of the characteristic for each point from the signals generated from the sample bottles;
   c. storing a list of the minimum intensity level for each point in the field by selecting the signal having the minimum value of the characteristic for each point from the signals generated from the sample bottles;
   d. generating the gray scale signals for a bottle being inspected;
   e. comparing the value of the characteristic of each gray scale signal for the bottle being inspected with the stored maximum and minimum intensity levels for the corresponding point in the field;
   f. accumulating a count total representing the number of gray scale signals for the bottle being inspected which have the value of the characteristic outside the range defined by the maximum and minimum intensity levels for the corresponding points in the field; and
   g. generating the reject signal when said count total exceeds a predetermined number corresponding to an acceptable label position.

19. The method according to claim 18 wherein step e. includes the step of generating a difference signal having a magnitude proportional to the difference between said gray scale signal characteristic value and said maximum intensity level magnitude when said signal characteristic value is greater than said maximum intensity level and the step of generating a difference signal having a magnitude proportional to the difference between said gray scale signal characteristic value and said minimum intensity level magnitude when said signal characteristic value is less than said minimum intensity level; and wherein step f. is performed by summing said difference signals as said count total.

20. The method according to claim 19 wherein step f. includes weighting said difference signals before they are summed.

* * * * *